United States Patent [19]

Silvian

[11] Patent Number: 4,944,299
[45] Date of Patent: Jul. 31, 1990

[54] HIGH SPEED DIGITAL TELEMETRY SYSTEM FOR IMPLANTABLE DEVICE

[75] Inventor: Sergiu Silvian, La Crescenta, Calif.

[73] Assignee: Siemens-Pacesetter, Inc., Sylmar, Calif.

[21] Appl. No.: 391,080

[22] Filed: Aug. 8, 1989

[51] Int. Cl.$^5$ .............................................. A61N 1/00
[52] U.S. Cl. ..................... 128/419 PG; 128/419 PT; 128/903; 455/100
[58] Field of Search .................. 128/419 PG, 419 PT, 128/903; 455/100

[56] References Cited

U.S. PATENT DOCUMENTS

| | | | |
|---|---|---|---|
| 4,262,632 | 4/1981 | Hanton et al. | 455/100 |
| 4,712,179 | 12/1987 | Heimer | 128/903 |
| 4,741,340 | 5/1988 | Batina et al. | 128/419 PT |

Primary Examiner—Francis Jaworski
Assistant Examiner—George Manuel
Attorney, Agent, or Firm—Bryant R. Gold; Lisa P. Weinberg; Leslie S. Miller

[57] ABSTRACT

A high speed digital telemetry system (10) includes a transmitter (12) and a receiver (14), at least one of which is adapted for use in an implantable device. The transmitter includes a data encoder (14), modulator (16), transmitting coil (20), and transmitting coil drive circuit (18). The data encoder examines prescribed incoming data bits and prior encoded data bits, generating an encoded data stream (36) that includes a data transition only when a prescribed correlation is noted amongst the examined bits. The modulator modulates a carrier signal (34) with the encoded data stream, causing a phase reversal of the carrier at each data transition of the encoded data stream. The transmitting coil drive circuit applies the modulated carrier (38) to the transmitting coil. The receiver includes a receiving coil (22) and associated amplifier (24) and bandpass filter (26) for detecting the transmitted modulated carrier. The bandpass filter is centered at the frequency of the carrier, passing the carrier only when no phase reversals are present. This results in an on-off signal at the frequency of the carrier. An AM detector (28) detects when the signal is present and when it is not, and appropriate decision logic (30) applies a suitable acceptance criteria to the detected signal to define the received binary data.

20 Claims, 4 Drawing Sheets

HIGH SPEED DIGITAL TELEMETRY SYSTEM FOR IMPLANTABLE DEVICE

BACKGROUND OF THE INVENTION

The present invention relates to a high speed digital telemetry system for use in an implantable device, such as an implantable pacemaker. More particularly, the present invention relates to an implantable high bit rate telemetry transmitter and corresponding external receiver that transmits data efficiently at a lower than Nyquist bandwidth.

Implantable devices are implanted in a human or animal for the purpose of performing a desired function This function may be purely observational or experimental in nature, such as monitoring certain body functions; or it may be therapeutic or regulatory in nature, such as providing critical electrical stimulation pulses to certain body tissue, nerves or organs for the purpose of bringing about a desired response. The modern implantable demand pacemaker is an example of an implantable device that performs both observational and regulatory functions, i.e., it monitors the heart to make sure it beats at appropriate times; and if not, it causes an electrical stimulation pulse to be delivered to the heart in an attempt to force the heart to beat at an appropriate rate.

In order for an implantable device to perform its functions at minimum inconvenience and risk to the person or animal within whom it is used, some sort of noninvasive telemetry means must be provided that allows data and commands to be easily passed back and forth between the implantable device and an external device. Such an external device, known by a variety of names, such as a controller, programmer, or monitor, provides a convenient mechanism through which the operation of the implantable device can be controlled and monitored, and through which data sensed or detected by the implantable device can be transferred out of the implantable device to an external (non-implanted) location where it can be read, interpreted, or otherwise used in a constructive manner.

As the sophistication and complexity of implantable devices has increased in recent years, the amount of data that must be transferred between an implantable device and its accompanying external device has dramatically increased. This, in turn, has resulted in a search for more efficient ways of effectuating such a data transfer. Any such system must, of course, not only transfer the desired data without significant error, but it must do so rapidly while preserving the limited power resources (e.g., a battery having a limited operating life) of the implanted device.

Heretofore, three basic techniques have been used for communicating with an implantable device: (1) static magnetic field coupling; (2) reflected impedance coupling; and (3) RF coupling. In static magnetic field coupling, a static magnetic field is generated external to the implanted device, e.g., using a permanent magnet, having sufficient strength to close (or open) a magnetic reed switch within the implanted device. While such a technique provides a fairly reliable mechanism for turning various functions within the implanted device ON or OFF, such as turning the telemetry circuits within an implanted device ON only when an external telemetry head is positioned a few inches from the implanted device, the technique is much too slow for efficiently transferring any significant amount of data. Further, for all practical purposes, the static magnetic system is useful only for transferring commands or data to the implanted device, not for transferring data or commands from the implanted device. This is because the weight and/or power requirements associated with the types of permanent magnets or electromagnets needed to operate a magnetic reed switch several inches distant therefrom is incompatible with the requirements of most implantable devices.

In a reflected impedance coupling system, information is transferred using the reflected impedance of an internal (implanted) L-R or L-C circuit energized by an inductively coupled, external L-R or L-C circuit. Such a system is shown, for example, in U.S. Pat. No. 4,223,679. Advantageously, such a system uses little or no current to transmit information. Disadvantageously, the speed at which the information is transferred is quite limited. The external circuit uses an RF (radio frequency) magnetic field carrier. In the cited patent, a voltage controlled oscillator (VCO), in the implanted device, is controlled by the signal to be telemetered. The VCO, in turn, varies the impedance that is reflected. If the signal controlling the VCO is a binary digital signal (having two possible values, e.g., a binary "1" and a binary "0"), this signal encodes the VCO so that the VCO varies from one frequency (representing a binary "1") to another frequency (representing a binary "0"). This technique is known as frequency shift keying (FSK). Each bit duration, i.e., the time in which the binary digit (bit) is expressed, requires a number of carrier cycles. Hence, the bit rate cannot generally be much higher than 10% to 30% of the VCO center frequency. On the other hand, the RF carrier frequency cannot be too high because of the metal enclosure of the implanted device acts as a low pass, single pole filter having an upper cut-off frequency of between 10-30 kHz. Further, the external oscillator L-C circuit typically has a Q (quality factor) of 20 to 50, meaning that the useful modulation bandwidth is limited to around 2 to 5 percent of the RF carrier frequency. This means that a 36 kHz carrier is typically only able to transmit data at a data rate of from 72 to 540 bits per second (bps). Such a rate is generally considered inadequate for modern implantable devices, which devices may have thousands or tens of thousands of bits of data to be transmitted.

In an RF coupled system, information is transferred from a transmitting coil to a receiving coil by way of a carrier signal. The carrier signal is modulated with the data that is to be transmitted using an appropriate modulation scheme, such as FSK or PSK (phase-shift keying—reversing the phase of the carrier by 180 degrees). The modulated carrier induces a voltage at the receiving coil that tracks the modulated carrier signal. This received signal is then demodulated in order to recover the transmitted data. Because of the metal enclosure of the implanted device, which acts as a low pass filter (attenuating high frequencies), the carrier frequency cannot be increased above approximately 10-20 kHz without an unacceptable increase in transmitting coil power. Further, depending upon the type of modulation/demodulation scheme employed, the data or bit rate cannot exceed a prescribed fraction of the carrier frequency, without exceeding a specified amount of mutual interference, i.e., without being able to reliably distinguish between a modulation that represents a binary "1" and modulation that represents a binary "0".

The maximum data transfer rate (bit rate) at which independent signal values can be transmitted over a specified channel without exceeding a specified amount of mutual interference is referred to as the "Nyquist rate." The maximum allowable Nyquist rate is directly related to the bandwidth of the channel through which the data is transferred. Conversely, the "Nyquist bandwidth" is that bandwidth required to allow independent signal values to be transmitted at a given rate without exceeding the specified levels of mutual interference. For example, if the bandwidth of the channel through which the data is transferred is W, the Nyquist rate (assuming an ideal channel) may be as high as 2W. Stated differently, if the data rate is 2W, the Nyquist bandwidth must be at least W. Because of these and other limitations, prior art implantable devices using RF coupling have generally not been able to transfer data at rates in excess of 2–4 kbps. (Note, that as used here and throughout this application, a one-sided bandwidth definition is used. That is, a bandwidth W refers to a range of frequencies from 0 to W, or from −W to 0. Where a carrier signal having a frequency $f_c$ is used, the one-sided bandwidth W refers to a range of frequencies from $f_c$ to $f_c+W$, or from $f_c-W$ to $f_c$.)

A further problem affecting the rate at which data can be transferred from an implantable device is electrical noise and/or EMI (electromagnetic interference). In particular, there are at least two primary sources of EMI associated with commonly used types of external devices that significantly affect the range of carrier frequencies and data rates that can be reliably and efficiently (at low power consumption levels) used to transfer data in an RF-type system. First, the input power line frequency (50–60 Hz) of the external device, and the associated switching magnetic fields (e.g., 30 Hz) used with a cathode ray tube (CRT) display, frequently used with external devices, create sufficiently large EMI harmonics to be troublesome as high as 2–6 kHz. Similarly, the 16 kHz line frequency of the horizontal scan of the cathode ray tube (CRT) commonly used with many electronic terminals, makes it extremely difficult to efficiently use a carrier frequency of 16 kHz or higher. In order to minimize the effect of such EMI on the transmission of data from an implanted device used in an environment where such interference is prevalent, and in order to maximize the speed at which the large amounts of data used with modern implantable devices may be transferred, it would thus be preferable to employ a narrow band telemetry channel (to filter out as much EMI and noise as possible) using a carrier signal in the 6–12 kHz range, and using a modulation scheme that permits a data bit rate as high as possible through such channel. While a telemetry system that increases the data bit rate of an implantable device up to an acceptably fast level has heretofore been proposed by the applicant herein, see U.S. Pat. application Ser. No. 07/085,914, filed 08/14/87, such was accomplished only at the expense of a wider bandwidth, thereby causing an increased susceptibility to EMI. What is needed, therefore, is an improved telemetry system for use with an implanted device that not only allows data to be transferred at an acceptably fast rate, e.g., 8 kHz, but that also allows the data at this fast rate to be transferred through a narrow bandwidth, thereby decreasing the susceptibility of the system to EMI and other noise sources. The present invention advantageously addresses this and other needs.

Further, the telemetry system described in the above-cited patent application utilizes an encoding scheme that requires the instantaneous frequency of a carrier signal applied to a transmitting coil to be suddenly changed or reversed. This is accomplished only at the expense of increased complexity in the modulation circuits and drive circuits that apply the modulated carrier signal to the transmitting coil. Such circuits, for example, employ two multiple capacitors that are switchably connected to the transmitting coil. A capacitor connected to the transmitting coil is needed to tune the transmitting coil to the correct frequency. Two capacitors are needed because the voltage applied to the coil by the drive circuits must regularly reverse its polarity, and it takes too much time, and is thus inefficient, for one capacitor to discharge one voltage polarity and charge to another each time that a reversal in the voltage applied to the coil occurs.

Unfortunately, as such telemetry circuits become more and more complex, more and more components are required for the circuits to perform their intended function. As the number of components increases, the cost of the circuit increases and the reliability of the circuit decreases. Therefore, in order to reduce the cost and improve the reliability, simpler and less complex circuits are needed. This is true not only in the implantable transmitter portion of the telemetry system, but also in the external receiver portion of the system where heretofore complex phase locked loops (PLL's) and similar complex circuits have been required in order to demodulate the recovered telemetry signal.

SUMMARY OF THE INVENTION

The present invention advantageously provides a telemetry system for use with an implantable device that allows a high bit rate to be transferred over a telemetry channel having a lower than Nyquist bandwidth. Advantageously, such a bit rate provides a significant improvement in the speed with which a given amount of data can be efficiently transferred from the implantable device to an external device. Moreover, by passing this higher bit rate through a bandwidth less than the Nyquist bandwidth, the system is able to tolerate a higher level of EMI.

In one embodiment, the present invention includes an implantable transmitter apparatus for transmitting digital binary data, comprising a sequence of input data bits, at a prescribed bit rate from an implantable device. The transmitter apparatus includes: (a) encoding means for converting the input sequence of data bits into an encoded binary data stream, comprising a sequence of encoded data bits, that includes an identifying mark when a prescribed correlation exits between the input data bits and the encoded data bits; (b) a transmitting coil circuit tuned to the prescribed bit rate; and (c) means for applying a carrier signal having a frequency equal to the prescribed bit rate to the transmitting coil circuit, including switching means for switching the phase of the carrier signal applied to the transmitting coil circuit by a prescribed amount for each identifying mark of the encoded binary data stream. Advantageously, when the prescribed correlation relates to a correlation between a current input data bit and a prior encoded data bit, it becomes possible to transmit the data over a channel having a lower than Nyquist bandwidth. In turn, this allows a significant improvement in the level of EMI rejection of the data transmission channel than has heretofore been possible.

In another embodiment, the present invention may be summarized as comprising a telemetry system for transferring binary digital data between an implantable device and an external device. This telemetry system includes: (1) a transmitter in either the implantable device or the external device, and (2) a receiver in the other device. The transmitter includes: (a) encoding means for generating an encoded data stream using an exclusive, or bit coding scheme, this bit coding scheme causing appropriate marks, such as a transition from one level to another, to be placed in the encoded data stream only when a prescribed correlation exists between prescribed data bits within the digital data to be transferred and the encoded data stream; (b) modulation means for modulating a carrier signal having a frequency $f_0$ with the encoded data stream; and (c) means for applying the modulated carrier signal to a transmitting coil. The receiver includes: (d) a receiving coil inductively coupled to the transmitting coil; (e) a bandpass filter coupled to the receiving coil, the bandpass filter having a bandwidth of less than $\frac{1}{2}f_0$ Hz that is centered at approximately $f_0$ Hz; (f) an AM detector coupled to the output of the bandpass filter; and (g) means coupled to the output of the AM detector to recreate the input data stream.

The invention may likewise be summarized as an efficient method of transferring a sequence of data bits to and from an implantable device at a high speed. This method comprises the steps of: (a) generating an encoded binary data stream that includes a transition only when a prescribed correlation exists between prescribed ones of the data bits within the sequence of data bits to be transferred and prior encoded data bits within the encoded binary data stream; (b) modulating a carrier signal with the encoded binary data stream; (c) applying the modulated carrier signal to a transmitting coil; (d) selectively connecting a capacitor in parallel with the transmitting coil in response to certain transitions of the encoded binary data stream, such as transitions in one direction (going from a low to a high level) and reversing the connection of the capacitor to the coil in response to certain other transitions of the encoded binary data stream, such as transitions in the other direction (going from a high to a low level); (e) inductively coupling a receiving coil to the transmitting coil, one of the transmitting coil or receiving coil being in the implantable device and the other being in an external device; (f) detecting the amplitude of only those components of the signal induced at the receiving coil having a frequency close to the frequency of the carrier signal; and (g) using the amplitude detected in step (f) to define the data that has been received. In practicing this method, it is noted that the capacitor connected in parallel with the transmitting coil forms an L-C circuit that is tuned to the carrier frequency, which carrier frequency may be the same as the bit rate at which the data is transferred. This capacitor is reversed in synchronism with reversing the phase of the carrier signal applied to the transmitting coil in order to preserve the charge on the capacitor, thereby avoiding the necessity of discharging the capacitor and recharging it to the opposite polarity, which discharging and recharging would consume additional power.

It is one aspect of the present invention to provide a high speed telemetry system that allows digital binary data to be efficiently transferred between an implantable device and an external device at a fast rate, and more particularly at a rate of around 8 kbps.

It is another aspect of the present invention to provide such a high speed telemetry system utilizing an encoding scheme and appropriate bandpass filtering that offers efficient bandwidth compression.

It is still another aspect of the invention to provide such a high speed telemetry system wherein the frequency of the carrier signal may be the same as the data transfer bit rate.

It is a further aspect of the invention to provide such a telemetry system having a bandwidth that is less than the Nyquist bandwidth, thereby significantly improving the immunity of the system to noise and EMI. For example, where the bit rate is 8 kbps, the bandwidth of the data transfer channel used with the present invention may advantageously be set to less than 4 kHz, e.g., 2 kHz, on each side of the 8 kHz carrier signal.

It is yet another aspect of the invention to provide such a telemetry system that is efficient to operate, requiring minimal operating power during a data transfer operation.

It is still a further aspect of the invention to provide a high speed telemetry system as above described wherein the data recovered at the receiver may be recovered using synchronous or asynchronous demodulation.

It is still another aspect of the invention to provide such a telemetry system that utilizes relatively few components, thereby making the system less expensive to manufacture and more reliable in its operation. In particular, one feature of the invention provides that only a single capacitor be used with the inductive coil as part of a transmitter L-C tuned circuit, even through the polarity of the voltage that is applied to the transmitting coil regularly reverses as part of the modulation of the carrier signal.

BRIEF DESCRIPTION OF THE DRAWINGS

The above and other aspects, advantages and features of the present invention will be more apparent from the following more particular description thereof, presented in conjunction with the following drawings, wherein.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the appended claims.

In the description of the invention that follows, like numerals or reference designators will be used to refer to like parts or elements throughout.

Figure 1:
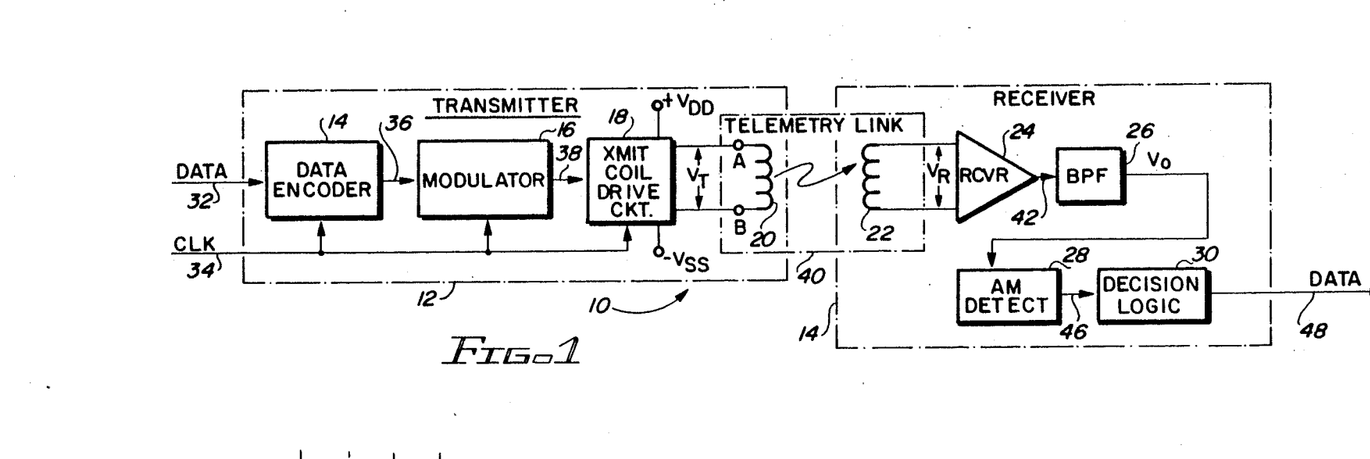
FIG. 1 is a block diagram of a high bit rate telemetry system in accordance with the present invention.

FIG. 1 shows a simplified block diagram of telemetry system 10 made in accordance with the present invention, and will be described first to present an overview of the elements included within the invention and its manner of operation. The telemetry system 10 includes a transmitter 12 and a receiver 14. The transmitter 12 includes a data encoder 14, a modulator 16, a transmit coil drive circuit 18, and a transmit coil 20. The receiver includes a receive coil 22, a receiver amplifier 24, a bandpass filter (BPF) 26, an AM detector 28, and decision logic 30. In a preferred embodiment, the transmitter 12 is included as part of an implantable device, and the receiver 14 is included as part of an external device. However, it is to be understood that these roles could be reversed, with the receiver being included in the implantable device and the transmitter being included in the external device. (It is noted that in a typical application, an implantable device includes both transmitting and receiving capabilities, as does its corresponding external device. However, different types of telemetry schemes or transmission principles are typically used to transfer data from the implanted device to the external device than are used to transfer data from the external device to the implanted device.)

The transmitter 12 receives as input signals a data signal, identified as DATA in FIG. 1, over an input signal line 32, and a clock signal, identified as CLK, over an input signal line 34. (Hereinafter, the signals appearing on these signal lines, as well as other signals appearing on other signal lines, may be referred to by the reference numeral of the signal line on which the signal appears, e.g., "the DATA signal 32," or "the clock signal 34.") As will be explained more fully below, the DATA signal 32 comprises a stream of binary data bits, typically in an NRZ (non-return-to zero) format (although other suitable binary formats could likewise be used) flowing at a given bit rate, $B_o$. An NRZ signal comprises a signal having two levels, with a first level representing a binary bit "1", and a second level representing a binary bit "0". If the bit rate $B_o$, for example, is 8000 bits per second (8 kbps), then one bit flows into the data encoder 14 over the data line 32 every 0.125 milliseconds (1/8000=0.000125).

The clock signal 34 will typically include a plurality of synchronized clock signals derived from a common clock signal source. These clock signals are shown in the block diagram of FIG. 1 as a single clock signal 34 for simplicity of presentation. At least one of these clock signals, typically comprising a square wave (although other suitable waveforms could be used, such as a pulse train), has a frequency equal to the bit rate $B_o$. As will be evident from the description presented below in connection with FIGS. 4 and 5, another one of these clock signals, used by a preferred embodiment of the present invention, has a frequency of $4B_o$.

In operation, the input data stream 32 is encoded in the data encoder 14, resulting in an encoded data stream that is presented to the modulator 16 over signal line 36 (hereafter "encoded data 36"). Advantageously, as set forth more fully below in the description of FIGS. 4 and 5, the preferred encoding scheme used by the data encoder 14, prepares the data in suitable form for transmission to the receiver through a channel having a narrow bandwidth without error propagation, as will be explained below. The preferred encoding scheme, which is explained more fully below in connection with FIG. 3A, analyzes prescribed bits of the input data 32 and known (prior) bits of the encoded data 36 for a prescribed correlation therebetween. When such a correlation is found, the next bit of the encoded data 36 assumes one value. When such a correlation is not found, the next bit of the encoded data 36 assumes another value. Said another way, an appropriate encoding mark, such as a data transition, appears in the encoded data 36 whenever a prescribed correlation is found to exist between specified bits of the incoming and prior encoded data.

The modulator 16 modulates an appropriate carrier signal using PSK (phase-shift-keying) modulation with the encoded data 36. The resulting PSK modulated carrier signal is applied to the transmit coil drive circuit 18 over signal line 38 (hereafter "modulated carrier 38"). The carrier signal has a frequency $f_0$, and is derived from the clock signal 34. It is preferred that the carrier signal have the same frequency as the input data stream. That is, $B_o = f_0$. In PSK modulation, the phase of the carrier signal is reversed 180 degrees for each change in the modulating signal. Thus, for the system shown in FIG. 1, and assuming a PSK modulation of the carrier, the modulated carrier signal 38 includes a phase reversal of the carrier signal for each encoding mark, such as a data transition, found in the encoded data 36.

The transmit coil drive circuit 18 applies the modulated carrier signal 38 to the transmit coil 20. This is achieved by selectively connecting positive and negative voltage supplies, $+V_{DD}$ and $-V_{SS}$, to respective sides of the coil 20. That is, at any given instant in time, the positive voltage supply $+V_{DD}$ may be applied to terminal a of the coil 20 at the same time that the negative voltage supply $-V_{SS}$ is applied to terminal b of the coil 20. When the phase of this signal is reversed, however, these connections are switched so that the positive voltage supply $+V_{DD}$ is applied to terminal b and the negative voltage supply $-V_{SS}$ is applied to terminal a, in effect reversing the polarity of the transmit voltage $V_T$ applied across the coil 20. This type of voltage switching requires careful timing considerations, as described more fully below in connection with FIGS. 4 and 5. Hence, one or more of the clock signals 34 is used to steer this switching operation.

Still referring to the simplified block diagram of FIG. 1, the operation of the receiver 14 will be described. With the transmit coil 20 energized, i.e., with a modulated carrier signal voltage $V_T$ applied thereto, and with the receive coil 22 inductively coupled to the transmit coil 20, a voltage $V_R$ is induced across the receive coil 22. The inductive coupling between the transmit coil 20 and the receive coil 22 thus forms a telemetry link 40 between the implanted coil (either the transmit coil 20 or the receive coil 22) and the external coil (the other coil). This inductive coupling may be considered similar to that observed in an air coil transformer. That is, if the transmit coil 20 is considered as a primary winding of an air coil transformer, and the receive coil 22 is considered as a secondary winding of this same transformer, then a voltage $V_T$ applied to the primary winding will be induced in and appear across the secondary winding as a voltage $V_R$. The voltage $V_R$ assumes substantially the same waveform shape as the voltage $V_T$, but with a significantly reduced amplitude, which amplitude is highly dependent upon the physical separation between the two coils.

The induced voltage $V_R$ is amplified in the receiver amplifier 24 and presented to a bandpass filter 26 over signal line 42 (hereafter the "amplified received signal 42"). The bandpass filter 26 has a frequency response substantially as illustrated in FIG. 3B. This frequency response has a bandwidth BW centered about the frequency $f_0$, the frequency of the carrier signal. Any frequencies outside of the passband are not passed through the filter 26. This is particularly advantageous for rejecting EMI caused by low frequency line frequencies, such as a 60 Hz power signal. Such EMI is illustrated in FIG. 3B by a series of decreasing amplitude spikes 61, representing the line frequency and its harmonics. The output signal of the bandpass filter output, $V_0$, is what is known as a "correlative or duobinary encoded data" signal, as the signal during one bit is dependent on that bit value and the prior bit value, this being the result of a narrow bandpass filter. (For a thorough description of correlative coding and duobinary techniques, see, e.g., M. Schwartz, *Information Modulation and Noise*, pp. 189–197, McGraw-Hill, 1980.) Those portions of the amplified received signal 42 that are close to the carrier signal frequency $f_0$ are readily passed through the bandpass filter 26. However, because the amplified received signal 42 includes a phase reversal of the carrier signal for each mark in the encoded data 36, and because such phase reversal represents an instantaneous frequency shift to roughly $2f_0$, significant portions of the amplified received signal 42 will not pass through the bandpass filter 26. The result is that the output signal of the bandpass filter, $V_0$, appears as an ON-OFF keyed signal, with some portions being ON and having a frequency of substantially $f_0$, and other portions being OFF (no signal present). As will be evident from the waveform timing diagram presented below in conjunction with FIG. 5, and using the precoding scheme shown, the pattern of the ON-OFF keying of the signal $V_0$ substantially tracks the pattern of the input DATA signal 32. Hence, by demodulating the signal $V_0$ in an appropriate manner, this data can be recovered.

FIG. 1 shows the bandpassed signal $V_0$ being applied to an AM detector circuit 28. The AM detector circuit detects the amplitude of the bandpassed signal $V_0$, which amplitude substantially tracks the informational content of the input DATA signal 32. The output of the AM detector circuit 28 is presented to appropriate decision logic 30 over signal line 46 (hereafter "AM detected signal 46"). The decision logic makes a decision as to whether the detected amplitude of the AM detected signal 46 at any given instant in time is representative of a binary "1" or a binary "0". Once this decision is made, a DATA output signal can be created and presented on signal line 48 (hereafter the "DATA output signal 48").

AM detector circuits and decision logic circuits are known in the art. The AM detector circuit 28 and the decision logic circuit 30 may take any of the common forms known in the art for such circuits. A simple AM detector circuit, for example, includes a diode, a capacitor and a resistor. Such a simple circuit, or equivalents thereof, when coupled to a simple decision logic circuit, such as a threshold circuit (e.g., a comparator circuit having a first input connected to the AM detected signal 46 and a second input connected to a voltage reference signal lying midway between the minimum and maximum voltage swings of the AM detected signal), offer the advantage of being able to detect the data asynchronously, i.e., without the need to recover a clock signal from amplified received signal 42. More complex AM detector circuits may, of course, also be used, including synchronous detector circuits that recover the clock signal of the data using a phase-locked loop (PLL), and that then carefully examine the contents of the AM detected signal each bit period (as determined by the recovered clock) to determine whether each bit represents a "1" or a "0".

Whether simple or complex circuits are used for the AM detector 28 and/or the decision logic 30, however, the primary function of the receiver 14 in accordance with the teachings of the present invention is to set the bandwidth of the telemetry channel through which the data passes. This it does by passing the amplified received data 42 through the bandpass filter 26, which bandpass filter has a narrow bandwidth BW centered about the carrier frequency $f_0$, as shown in FIG. 3B. Because of the particular encoding scheme employed in the transmitter, it is possible for the bandwidth BW to be significantly narrower than the Nyquist bandwidth (which Nyquist bandwidth must be at least $\frac{1}{2}f_0$. This narrow or compressed bandwidth advantageously improves the immunity of the system to EMI or other noise, i.e., the signal-to-noise ratio (S/N) is vastly improved.

Figure 2:
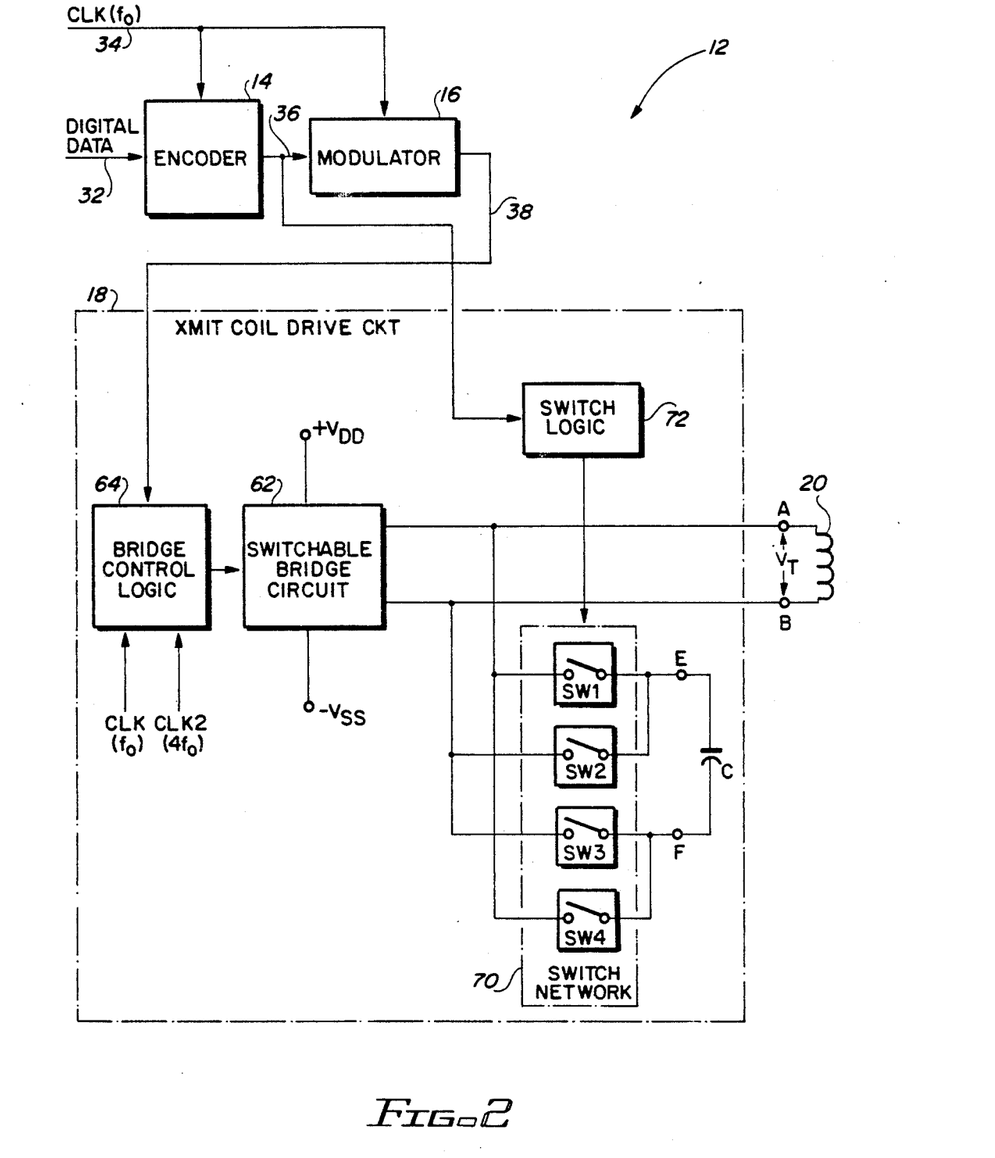
FIG. 2 is a more detailed block diagram of the transmitter portion of the telemetry system of FIG. 1.

Referring next to FIG. 2, a more detailed block diagram of the transmitter 12 of the present invention is shown. As shown in FIG. 2, the encoder 14 preferably comprises an encoder that performs the encoding operation $d_k = x_k + d_{k-1}$, where $d_k$ is the encoder output at the k bit time, $d_{k-1}$ is the encoder output at the prior bit time, and $x_k$ is the data input at the k bit time. Advantageously, when such an encoding scheme is used, and when one considers the filtering process carried out by the bandpass filter 26, it is seen that the most significant property of this type of encoding and filtering, termed the correlative or duobinary process, is that it affords a two-to-one bandwidth compression relative to binary signaling; or equivalently, for a fixed bandwidth, it has twice the speed capability in bits per second compared with a binary system. This it does by examining successive sequences of two overlapping binary bits. For example, referring momentarily to FIG. 3A, a representative input DATA signal 32 is illustrated. This input DATA signal comprises a sequence of NRZ binary bits "110110001110". In accordance with the described encoding process used by the present invention, a first bit of the incoming data (32) is examined relative to a prior bit of the encoded data (36). The next bit of the encoded data is set according to the above mentioned encoding equation.

The prescribed encoding between the specified bits in accordance with a preferred embodiment of the present invention is that the two bits (the current incoming data bit and the prior encoded data bit) must be different in order to generate a "1". Such a difference is readily determined using an Exclusive OR logic gate, or by performing a modulo-two sum of the two bits.

Figure 3A:
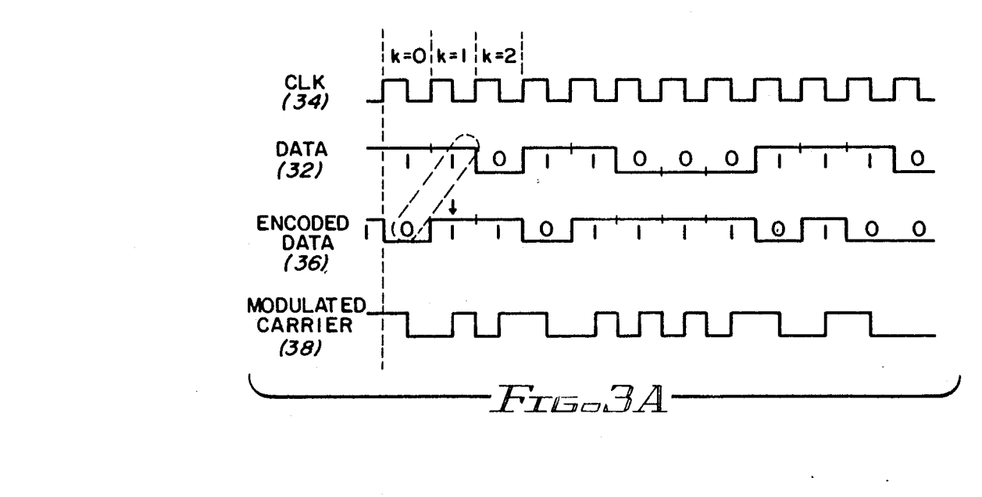
FIG. 3A is a waveform diagram and illustrates a preferred manner of encoding digital binary data in accordance with present invention.
Figure 3B:
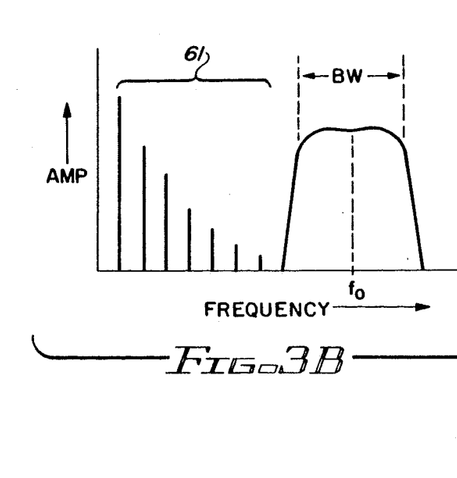
FIG. 3B illustrates the preferred frequency response of the bandpass filter of FIG. 1.

To illustrate, referring to the two bits circled by the dashed line in FIG. 3A, the data bit at time k=1 for the incoming data sequence is a "1". The encoded data bit at the previous bit time (k=0) is a "0". The modulo-two sum of these two bits is a "1". Hence the encoded data bit at the current bit time is set to be a "1", as indicated by the arrow pointing to the "1" of the encoded data at bit time k=1.

By applying the correlation criteria specified above (determining the modulo-two sum of the current data bit with the prior encoded bit) to the bit sequences shown in FIG. 3A, it is seen that the encoded data signal 36 comprises a bit sequence of "01101111010" for the input data bit sequence shown. Note that the transitions (changes from a low level to a high level, or from a high level to a low level) in the encoded data signal 36 are synchronized with appropriate transitions of the basic clock signal 34.

The transitions (or equivalent marks) in the encoded data signal 36 are important because, in accordance with the teachings of the present invention, the phase of the carrier signal applied to the coil 20 is reversed for each transition of the encoded data signal 36. A carrier signal modulated in this manner is also shown in FIG. 3A, and identified as the modulated carrier 38. Note that the carrier signal may simply be the clock signal 34 used to clock the input data signal 32 into the encoder 14. This clock signal has a frequency $f_0$ which is equal to the bit rate $B_0$.

The modulated carrier (clock) signal 38 is applied to the transmit coil drive circuit 18 in order to effectuate a phase reversal of the voltage $V_T$ applied across the coil 20. As illustrated in FIG. 2, the transmit coil drive circuit 18 includes a switchable bridge circuit 62 connected to the coil 20 and the positive and negative voltage supplies $+V_{DD}$ and $-V_{SS}$. This switchable bridge circuit is controlled by bridge control logic 64. The bridge control logic, in turn, is controlled by the modulated carrier signal 38 and two other clock signals: CLK (having a frequency of $f_0$) and CLK2 (having a frequency of $4f_0$). The drive circuit 18 further includes a capacitor C connected in parallel with the coil 20 through a switch network 70. The switch network 70, in turn, is controlled by switch logic 72. Switch logic 72 is controlled by the encoded data signal 36.

In operation, the bridge control logic turns ON appropriate branches of the switchable bridge circuit 62 for a short time subsequent to each transition of the modulated carrier signal, thereby connecting the appropriate side of the coil 20 to the appropriate voltage potential during this time. Further, as will be evident from the description of FIGS. 4 and 5 presented below, the bridge control logic reverses the polarity of the voltages applied to the coil 20 during this short time whenever a transition appears in the encoded binary data 36.

The switch network 70 includes four switches SW1, SW2, SW3, and SW4. Switches SW1 and SW3 are controlled to close and open together. When closed, they connect sides E and F of capacitor C to sides A and B of coil 20, respectively. Similarly, switches SW2 and SW4 are controlled so as to close and open together. When closed, they connect sides E and F of capacitor C to sides B and A of coil 20, respectively. The closure of these two pairs of switches is mutually exclusive, so that SW1 and SW3 cannot be closed at the same time that SW2 and SW4 are closed, and vice versa. The alternate closure and opening of these pairs of switches thus inverts the connection of the capacitor across the coil 20. This switching occurs in synchrony with a polarity change of the voltage applied to the coil, at a time when the capacitor C is charged to a maximum voltage of one polarity. Hence, the charge on the capacitor is reversed at the same time that the voltage applied to the coil is reversed. This action preserves the charge on the capacitor, thereby conserving energy.

The value of the capacitor C is selected to create a tuned circuit with the inductance of the coil 20 at the carrier frequency $f_0$. Advantageously, only a single capacitor C is required for this purpose, rather than multiple capacitors as have been required in similar circuits of the prior art.

Figure 4:
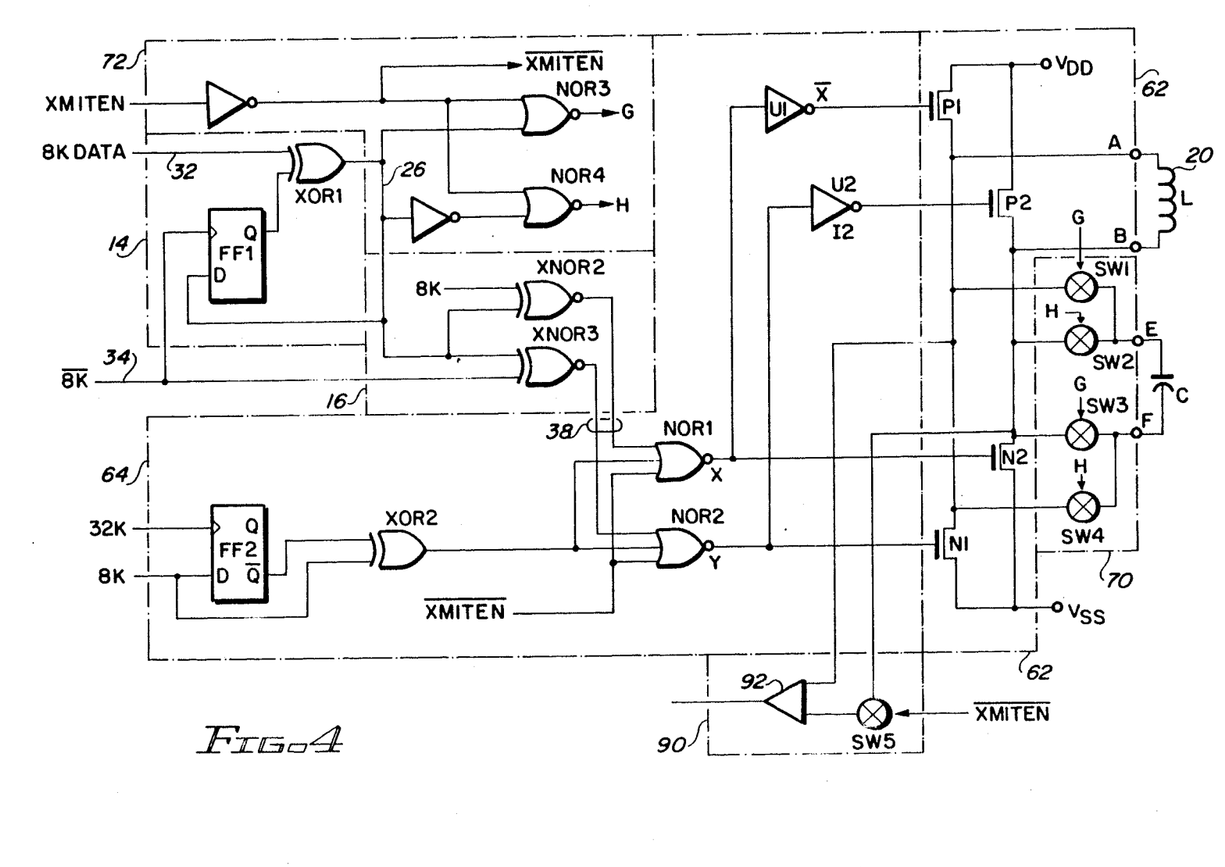
FIG. 4 is a logic schematic diagram of the transmitter shown in FIG. 2.
Figure 5:
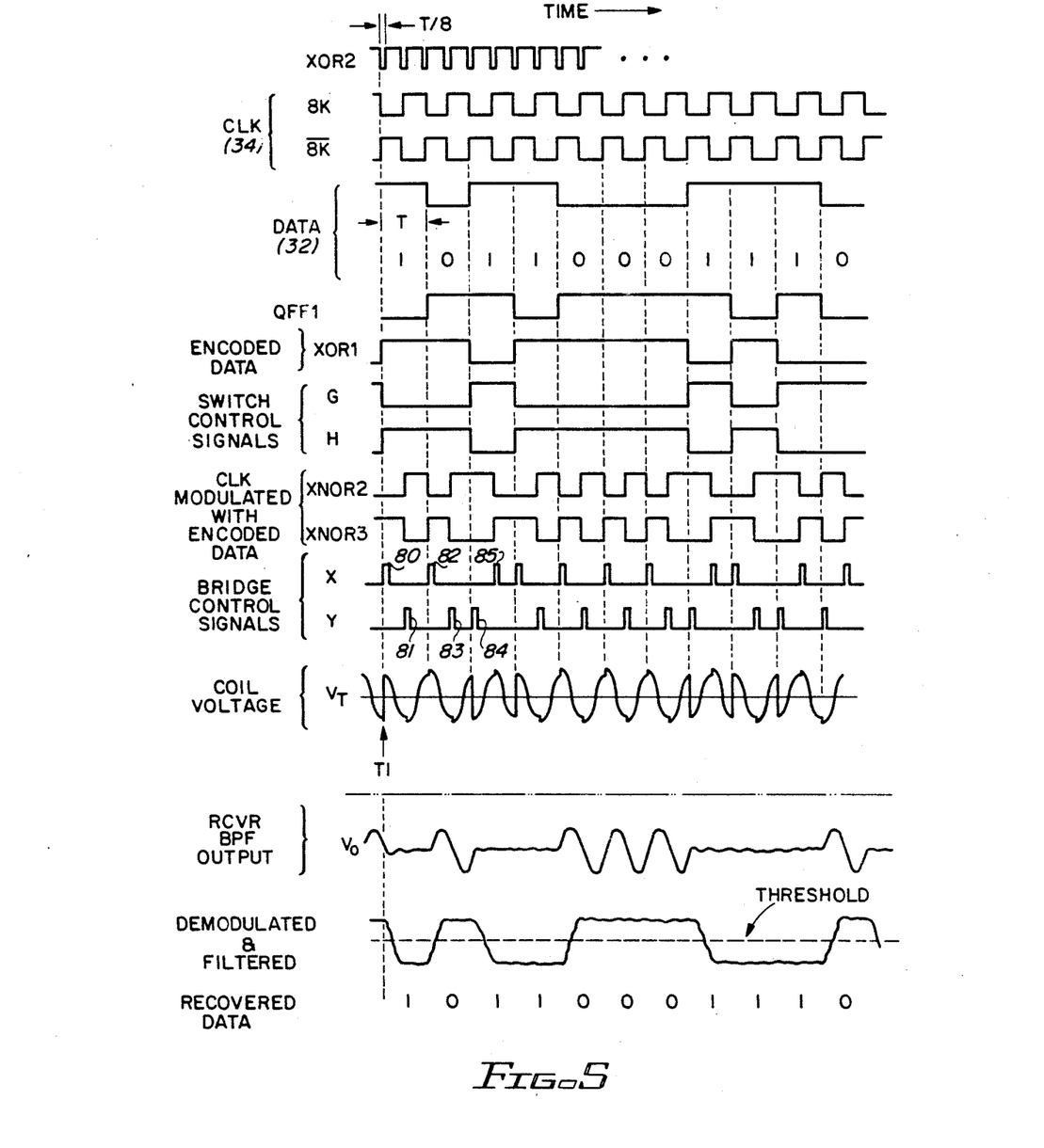
FIG. 5 is a waveform timing diagram that illustrates key signals associated with the operation of the telemetry system of the present invention.

FIG. 4 shows a logic diagram of the transmitter circuit 12 of the present invention. FIG. 5 is a timing diagram that illustrates some of the key signals associated with the operation of the circuit of FIG. 4. As seen in FIG. 4, the encoder 14 comprises a D flip flop FF1 and an Exclusive OR gate XOR1. One input to the gate XOR1 is the input DATA signal 32. As indicated in FIG. 5, this DATA has a bit period of T, and a bit rate of 1/T. In the preferred embodiment, the bit rate is approximately 8 kbps. The other input to the gate XOR1 is the Q output of the flip flop FF1. The flip flop FF1 is clocked by the inverse clock signal 34, which inverse clock signal also has a rate of 1/T, and is synchronized with the data bit transitions. The data input terminal of FF1 is the output of the gate XOR1, which output comprises the encoded data 36. As thus configured, the encoded data 36 is equal to the modulo-2 sum of the input data at bit time t=k and the output data (encoded data 36) at bit time t=k−1 (the previous bit time).

The modulator 16 is realized using a pair of two-input exclusive NOR gates, XNOR1 and XNOR2. The encoded data signal 36 is applied to one input of each of these exclusive NOR gates. The other input of gate XNOR1 is connected to the clock signal having a rate 1/T, while the other input of gate XNOR2 is connected to the inverse of the clock signal having a rate 1/T. As seen in the timing diagram of FIG. 5, the output signals 38 of the two gates XNOR1 and XNOR2 thus comprise complimentary carrier signals at rate 1/T that change phase each time the encoded data signal 36 changes state.

The bridge control logic 64 includes logic circuitry for generating narrow control pulses, identified as X and Y in FIGS. 4 and 5, that are used to switch the switchable bridge circuit 62. These control pulses are generated by first generating a stream of narrow pulses using flip flop FF2 and exclusive OR gate XOR2. The clock applied to FF2 is at a rate 4/T, or approximately 32 KHz, assuming T=0.125 msec. The basic clock signal, having a frequency 1/T is applied to the data input of FF2 This same clock signal is applied to one of the two inputs of the gate XOR2, while the other input is connected to the inverted Q output of FF2. As shown by the signal labeled XOR2 in FIG. 5, this arrangement causes the output signal of XOR2 to be a train of negative pulses of width T/8 at a base rate 2/T, with the leading edge of each pulse coinciding with the edges of the basic clock signal 34.

At the heart of the bridge control logic 64 are two three-input NOR gates NOR1 and NOR2. One input of both gates is attached to the inverse of a transmit enable signal, which transmit enable signal is identified as XMITEN. When the XMITEN signal is high (XMITEN inverse low), the gates NOR1 and NOR2 are enabled. When the XMITEN signal is low (XMITEN inverse high), the gates NOR1 and NOR2 are disabled.

With the XMITEN signal high, and hence with gates NOR1 and NOR2 enabled, the state of the other two input signals to each gate determine their respective outputs, X and Y. Only when all three inputs to each gate are low, does the output go high. Otherwise, the output remains low. One input to both gates NOR1 and NOR2 is the narrow negative pulses obtained from the output of XOR2. Hence, the output signals X and Y can only go high when these negative pulses go low and when the other input to the gates NOR1 and NOR2 is low. The other input to the gate NOR1 is the output from XNOR2 (the modulated carrier signal 38). The other input to the gate NOR2 is the output from XNOR3 (the inverted modulated carrier signal 38). Thus, when the modulated carrier signal is low, one of the output signals X or Y, but never both signals, produces a positive going pulse coincident with the corresponding negative pulse applied to the inputs of NOR1 and NOR2.

The X and Y signals thus generated are illustrated in the timing diagram of FIG. 5. Note that a pulse of duration T/8 appears on one of these signals every T/2 seconds, where T is the bit duration and 1/T is the frequency of the carrier signal (and clock signal 34). It is noted that a pulse width of T/8 is only exemplary, and other narrow pulse widths (narrow relative to T) could also be used. For a given phase of the modulated carrier signal, these pulses alternate between the X and Y signals, e.g., with a first pulse 80 appearing on X, a second pulse 82 appearing on Y at a time T/2 seconds later, a third pulse 82 appearing on X at a time T seconds later, and a fourth pulse 83 appearing of Y at a time 2T later, and so on. When the phase of the carrier signal reverses, the order in which these pulses appears also reverses. That is, a fifth pulse 84 appears on the Y signal at a time T/2 after the fourth pulse 83. A sixth pulse 85 appears on the X signal at a time T/2 after the pulse 84. This process continues, with a pulse occurring every T/2 seconds, and with the order of the pulses reversing for each phase reversal of the carrier.

The pulse control signals X and Y (and their respective inverse signals, generated by invertor gates U1 and U2), are applied to the switchable bridge circuit 62. The switchable bridge circuit 62 includes four transistor switches, identified in FIG. 4 as P1, P2, N1 and N2. The switches P1 and P2 are turned ON by applying a low signal to their respective gate terminals, and the switches N1 and N2 are turned ON by applying a high signal to their respective gate terminals. Hence, when a positive pulse is present on the X signal, turning switch N2 ON, a negative pulse appears at the switch P1 (by virtue of the invertor U1), turning switch P1 ON. In this way, switches P1 and N2 are always turned ON together when a pulse appears on the X signal. Similarly, switches P2 and N1 are always turned ON when a pulse appears on the Y signal. Significantly, because of the manner in which the X and Y control pulses are always separated in time by T/2 seconds, it is not possible for switches P1 and N2 to be ON at the same time that switches P2 and N1 are ON.

Still referring to FIG. 4, it is seen that the switch network 70 connects the capacitor C in parallel with the coil 20 through four switches, SW1, SW2, SW3, SW4. These switches are solid state switches that are controlled by the logic signals G and H. The logic signals G and H, in turn, are generated by switch logic 72. Switch logic 72 includes two two-input NOR gates, NOR3 and NOR4. One input to each of these gates is connected to the inverse transmit enable signal XMITEN. The other input to NOR3 is connected to the encoded data signal 36. The other input to NOR4 is connected to the inverse of the encoded data signal 36. When enabled by the transmit enable signal, the logic signals G and H are the same as the data signal 36 (G) or the inverse of the data signal 36 (H). Thus, when logic signal G turns ON switches SW1 and SW3, logic signal H turns OFF switches SW2 and SW4. Similarly, when logic signal H turns ON switches SW2 and SW4, logic signal G turns OFF switches SW1 and SW3. As explained above in connection with FIG. 2, these switches connect sides E and F of the capacitor C to sides A and B, respectively, of the coil 20 when SW1 and SW3 are turned ON; and connect sides E and F of the capacitor C to sides B and A, respectively, of the coil 20 when SW2 and SW4 are turned ON. Unlike the control pulses X and Y, the control signals G and H are continuous, meaning that the capacitor C is always connected to the coil 20 through one pair of these switches (SW1 and SW3, or SW2 and SW4).

With switches P1 and N2 ON (and switches P2 and N1 OFF), the positive voltage supply $+V_{DD}$ is connected through switch P1 to side A of the coil 20, and the negative voltage supply $-V_{SS}$ is connected through switch N2 to side B of the coil 20. With switches P2 and N1 ON (and switches P1 and N2 OFF), the negative voltage supply $-V_{SS}$ is connected through switch P2 to side A of the coil 20, and the positive voltage supply $+V_{DD}$ is connected through switch N1 to side B of the coil 20.

Referring to the timing diagram of FIG. 5, it is thus seen that at time T1, the X control pulse 80 turns on switches P1 and N2, thus forcing the voltage $V_T$ across the coil 20, measured at side A relative to side B, to be positive. (The voltage across an inductor can change instantaneously, while the current through the inductor cannot.) At this same time T1, the capacitor C is connected in parallel with the coil 20 by switches SW2 and SW4, and is disconnected from the coil 20 by switches SW1 and SW3. Prior to time T1, the capacitor C had been charged such that side E was negative relative to side F (or, alternatively, side F was positive relative to side E). At time T1, side F (the positively charged side) of the capacitor C is connected to side A of the coil (connected to the positive voltage supply through P1) through SW4, and side E (the negatively charged side) is connected to side B of the coil (connected to the negative voltage supply through N2) through SW2. This action preserves the charge on the capacitor C, thereby saving energy. The positive and negative supplies are connected to the coil in this fashion for only a short time, e.g., T/8 seconds, after which time the coil is disconnected from the voltage supplies. The capacitor C, however, with its positive charge, remains connected to the coil 20. Once the voltage supplies have been disconnected, the coil and the capacitor function as an L-C circuit, with the voltage $V_T$ across the coil decreasing as the current flowing through the coil (obtained from the charge on the capacitor) increases.

When the voltage across the coil has decreased a maximum amount, at a time T/2 later, the Y control pulse 81 causes the positive and negative voltage supplies to be connected to the B and A sides of the coil, respectively, for a short time. The voltage across the coil at this time (A relative to B) is already negative, as is the charge of the capacitor. Thus, the L-C circuit operation continues as described above, only this time the voltage $V_T$ across the coil decreases from its negative value to a positive value. By a time T seconds after T1, the coil voltage is again positive, as indicated in FIG. 5, completing one full cycle of the carrier signal. Another cycle of the carrier signal is applied to the coil 20 in a similar manner, as controlled by the control pulses 82 and 83. After this second cycle, the phase of the carrier signal is reversed. As a result, the control pulse 84 applies a negative voltage to the coil 20, causing the voltage across the coil to immediately switch. Further, at this phase reversal time, when the G and H control signals change polarity, the connection of the capacitor C relative to the coil is reversed. This operation continues, with the PSK modulated carrier signal being applied to the transmit coil 20, as indicated in the timing diagram of FIG. 5.

Still referring to the waveforms of FIG. 5, and also referring to the block diagram of the receiver 14 in FIG. 1, the coil voltage $V_T$ is coupled to the receive coil 22 and amplified by receiver amplifier 24. The amplified receive coil voltage 42 is substantially the same as the transmit coil voltage $V_T$. That is, the modulated carrier signal is coupled through the receive coil and amplified by the receiver amplifier 24. When this signal is applied to the bandpass filter 26, only those frequency components near the bandpass frequency $f_0$ pass therethrough without attenuation. Because every 180 degree phase shift of the modulated carrier is equivalent to an instantaneous shift in the frequency of the carrier, those portions of the carrier immediately after a phase shift are not passed through the bandpass filter. As seen in FIG. 5, it takes about one cycle after for every phase shift before the signal begins to pass through the bandpass filter. Thus, the output signal from the bandpass filter, $V_0$, has portions thereof that include the carrier signal at frequency $f_0$, and portions that include no carrier signal. This signal can then be amplitude detected in conventional manner, either synchronously or asynchronously, in order to recover the data information therefrom.

Also shown in FIG. 4, in addition to the transmitter logic/schematic diagram, is a receiver 90. This receiver includes an amplifier 92 that is connected to sides A and B of coil 20 through a switch SW5. When the transmit enable signal has disabled the transmit portions of the circuit, i.e., when the transmit enable signal is low (inverse of transmit enable is high), a switch SW5 connects side B of the coil 20 to one of the inputs of the receive amplifier 92. In this state, signals coupled to the coil 20 from an external coil can be received and routed to appropriate circuitry used within the device. In this manner, the coil 20 can serve both as a transmit coil when the device is operating in a transmit mode, and as a receive coil when the device is operating is a receive mode, the transmit and receive modes being defined by the transmit enable signal.

In the preferred embodiment of the present invention, the frequency of the carrier signal is the same as the desired bit transfer rate, e.g., 8192 Hz or bps. At this bit rate, the bandwidth of the bandpass filter may be less than 4000 Hz, e.g., as narrow as 2000 Hz. Using a narrow bandwidth provides a significant improvement in the noise and EMI immunity. The coil 20 has an inductance of approximately 0.5 henries, and the capacitor C has a value of 680 pf. The transistor switches P1 and P2 may be realized with any suitable P-channel MOSFET, or equivalent device, while the transistor switches N1 and N2 may be realized with any suitable N-channel MOSFET, or equivalent device. Similarly, any of numerous commercially available solid state switches can be used for the switches SW1, SW2, SW3, SW4 and SW5. The entire system uses few components and requires minimal adjustments. Where low power CMOS logic gates are employed, the system consumes little power.

A high speed telemetry system has thus been described that allows digital binary data to be efficiently transferred between an implantable device and an external device at a fast rate, such as 8192 bps. Further, and most significantly, the system utilizes an encoding scheme that allows for significant bandwidth compression. This bandwidth compression allows a bandwidth to be used that is less than the Nyquist bandwidth, thereby significantly improving the immunity of the system to noise and EMI. Moreover, the system described is simple, requiring few components, and is efficient to operate, requiring minimal operating power during a data transfer operation. Finally, the system is flexible and permits recovery of data using either synchronous or asynchronous demodulation.

While the invention described herein has been described with reference to a particular embodiment and application thereof, numerous variations and modifications could be made thereto by those skilled in the art without departing from the spirit and scope of the invention as claimed. Accordingly, the true scope of the invention should be determined with reference to the claims set forth below.

What is claimed is:

1. Implantable transmitter apparatus for transmitting digital binary data at a prescribed bit rate from an implantable device, said digital binary data comprising a sequence of incoming data bits, said transmitter comprising:
   encoding means for converting said sequence of incoming data bits into an encoded binary data stream, comprising a sequence of encoded data bits, that includes an identifying mark only when a prescribed correlation exists between prescribed ones of said incoming data bits and encoded data bits;
   a transmitting coil circuit tuned to said prescribed bit rate; and
   means for applying a carrier signal having frequency equal to said prescribed bit rate to said transmitting coil circuit, including switching means for switching the phase of the carrier signal applied to said transmitting coil circuit by a prescribed amount for each identifying mark of said encoded binary data stream.

2. Apparatus as set forth in claim 1 wherein said prescribed correlation between prescribed ones of said incoming and encoded data bits comprises a prescribed relationship between a current incoming data bit and a prior encoded data bit.

3. Apparatus as set forth in claim 2 wherein said prescribed relationship exists when said current incoming data bit and said prior encoded data bit are different.

4. Apparatus as set forth in claim 2 wherein said encoded binary data stream comprises a binary signal having only two states, and wherein said identifying mark placed in said encoded binary data stream comprises a transition from one of its states to the other state.

5. Apparatus as set forth in claim 1 wherein said transmitting coil circuit comprises an LC circuit tuned to the prescribed bit rate; said LC circuit including
   an inductor;
   a capacitor; and
   switching circuit means for selectively connecting said capacitor to said inductor, a first and second side of said capacitor being connected to a first and second side of said inductor, respectively, in accordance with a first connection scheme of said switching circuit means; and the first and second side of said capacitor being connected to the second and first side of said inductor, respectively, in accordance with a second connection scheme of said switching circuit means.

6. Apparatus as set forth in claim 5 wherein said switching circuit means comprises a plurality of switches, said plurality of switches causing the connections of said first and second connection schemes to be realized in response to the identifying marks in said encoded binary data stream.

7. Apparatus as set forth in claim 6 wherein said means for applying the carrier signal to said transmitting coil circuit includes a bridge circuit that selectively connects positive and negative voltage potentials to: (a) the first and second sides, respectively, of said inductor during prescribed first portions of each cycle of said applied carrier signal, and (b) the second and first sides, respectively, of said inductor during prescribed second portions of each cycle of said applied carrier signal.

8. Implantable transmitter apparatus for transmitting digital binary data at a prescribed bit rate from an implantable device, said digital binary data comprising an input sequence of data bits, said transmitter comprising:
  encoding means for converting said input sequence of data bits into an encoded binary data stream, comprising a sequence of encoded incoming data bits, that includes an identifying mark only when a prescribed correlation exits between prescribed ones of said incoming data bits and encoded data bits;
  modulator means for modulating a carrier signal at said prescribed bit rate with said encoded binary data stream;
  a transmitting coil circuit tuned to said prescribed bit rate, said transmitting coil circuit including an inductor, a capacitor, and a switching circuit selectively connecting said capacitor to said inductor, a first and second side of said capacitor being connected to a first and second side, respectively, of said inductor in accordance with a first connection scheme of said switching circuit, and the first and second side of said capacitor being connected to the second and first side, respectively, of said inductor in accordance with a second connection scheme of said switching circuit, the first and second connection schemes of said switching circuit being defined in response to said identifying marks in said encoded binary data stream; and
  means for applying said modulated carrier signal to said transmitting coil circuit.

9. Apparatus as set forth in claim 8 wherein said prescribed correlation between prescribed ones of said incoming and encoded data bits comprises a prescribed relationship between an incoming data bit and a previously existing encoded data bit.

10. A telemetry system for transferring binary digital data between an implantable device and an external device comprising:
  a transmitter including
    encoding means for generating an encoded data stream from an input data stream of binary bits to be transferred, said encoded data stream being encoded using a bit coding scheme that places appropriate marks in the encoded data stream only when a prescribed correlation exists between prescribed data bits of said input data stream and encoded data stream;
    modulation means for modulating a carrier signal having a frequency $f_0$ with said encoded data stream,
    means for applying said modulated carrier signal to a transmitting coil; and
  a receiver including
    a receiving coil inductively coupled to said transmitting coil,
    a bandpass filter coupled to said receiving coil, said bandpass filter having a bandwidth of less than $f_0$ Hz that is centered at approximately $f_0$ Hz,
    a detector coupled to the output of said bandpass filter, and
    means coupled to the output of said detector to recreate therefrom said data stream;
  one of said transmitter or receiver being in said implantable device and the other being in said external device.

11. The telemetry system as set forth in claim 10 wherein said prescribed correlation that must exist between prescribed data bits of said input data stream and said encoded data stream comprises a difference between a current data bit of the incoming data stream and a prior data bit of the encoded data stream.

12. The telemetry system as set forth in claim 10 wherein said modulation means comprises means for switching the phase of the carrier signal 180 degrees for each mark in the encoded data stream.

13. The telemetry system as set forth in claim 12 wherein said encoded data stream comprises a digital signal having two levels, and wherein the mark placed in said encoded data stream by said encoding means comprises a transition between said two levels.

14. The telemetry system as set forth in claim 12 wherein said means for applying said modulated carrier signal to said transmitting coil comprises
  a bridge drive circuit for selectively connecting positive and negative voltage potentials to respective sides of said transmitting coil in response to bridge control signals; and
  bridge control logic means for generating said bridge control signals in synchrony with transitions of said carrier signal and in response to said encoded data stream.

15. The telemetry system as set forth in claim 14 further including
  a capacitor, and
  a switching circuit selectively connecting said capacitor to said transmitting coil, a first and second side of said capacitor being connected to a first and second side, respectively, of said transmitting coil in accordance with a first connection scheme of said switching circuit, and the first and second side of said capacitor being connected to the second and first side, respectively, of said transmitting coil in accordance with a second connection scheme of said switching circuit, the occurrence of a mark in said encoded data stream causing said switching circuit to change from one of said first or second connection schemes to the other of said first or second connection schemes.

16. A method of transferring a sequence of data bits to and from an implantable device at a prescribed bit rate comprising:
  (a) generating an encoded binary data stream that includes an identifiable mark therein only when a prescribed correlation exists between prescribed ones of the data bits within said sequence of data bits to be transferred and prior encoded data bits within the encoded binary data stream;

(b) modulating a carrier signal with said encoded binary data stream;

(c) applying said modulated carrier signal to a transmitting coil;

(d) selectively connecting a capacitor in parallel with said transmitting coil in response to the transitions of said encoded binary data stream in one direction, and reversing the connection of said capacitor to said coil in response to the transitions of said encoded binary data stream in the other direction;

(e) inductively coupling a receiving coil to said transmitting coil, one of said transmitting coil or receiving coil being in the implantable device and the other being in an external device;

(f) detecting the amplitude of only those components of the signal induced at the receiving coil having a frequency close to said prescribed bit rate; and (g) using the amplitude detected in step (f) to define the data that has been received.

17. The method as set forth in claim 16 wherein step (g) comprises demodulating the detected amplitude asynchronously.

18. The method as set forth in claim 16 wherein step (g) comprises recovering a clock signal from the signal induced at the receiving coil, and demodulating the detected amplitude synchronously with said clock.

19. The method of claim 16 wherein step (a) comprises placing a mark within said encoded binary data stream only when there is a difference between a prescribed bit of the sequence of data bits to be transferred and a prescribed previously generated bit of the encoded binary data stream.

20. The method of claim 16 wherein step (a) comprises performing a modulo-two sum of a prescribed bit of the sequence of data bits to be transferred and a prescribed previously generated bit of the encoded binary data stream, and causing a mark to be placed in said encoded binary data stream only when said modulo-two sum is one.

* * * * *